(12) United States Patent
Knyrim

(10) Patent No.: US 8,671,739 B2
(45) Date of Patent: Mar. 18, 2014

(54) INDICATOR MATERIAL AND INDICATOR DEVICE COMPRISING SAID INDICATOR MATERIAL

(75) Inventor: Johanna Knyrim, München (DE)

(73) Assignee: Clariant Prosukte (Deutschland) GmbH, Frankfurt am Main (DE)

( * ) Notice: Subject to any disclaimer, the term of this patent is extended or adjusted under 35 U.S.C. 154(b) by 580 days.

(21) Appl. No.: 12/965,035

(22) Filed: Dec. 10, 2010

(65) Prior Publication Data

US 2012/0144906 A1    Jun. 14, 2012

(30) Foreign Application Priority Data

Dec. 10, 2010   (EP) ..................................... 10194491

(51) Int. Cl.
*G01N 21/81* (2006.01)
*G01N 21/78* (2006.01)

(52) U.S. Cl.
USPC ............................ 73/29.04; 116/206; 604/361

(58) Field of Classification Search
USPC ............. 73/29.04, 73, 74, 75, 76, 77, 335.01; 156/308.4; 116/206
See application file for complete search history.

(56) References Cited

U.S. PATENT DOCUMENTS

| | | |
|---|---|---|
| 2,214,354 A | 9/1940 | Snelling |
| 2,249,867 A | 7/1941 | Snelling |
| 2,460,065 A | 1/1949 | Davis |
| 2,460,066 A | 1/1949 | Davis |
| 2,460,067 A | 1/1949 | Davis |
| 2,460,068 A | 1/1949 | Davis |
| 2,460,069 A | 1/1949 | Davis |
| 2,460,070 A | 1/1949 | Davis |
| 2,460,071 A | 1/1949 | Davis |
| 2,460,072 A | 1/1949 | Davis |
| 2,460,073 A | 1/1949 | Davis |
| 2,460,074 A | 1/1949 | Davis |
| 2,526,938 A | 10/1950 | Davis et al. |
| 2,580,737 A | 1/1952 | Davis |
| 2,627,505 A | 2/1953 | Goodwin et al. |
| 2,716,338 A | 8/1955 | Blinn |
| 3,084,658 A | 4/1963 | Schell |
| 3,680,364 A | 8/1972 | Carrier |
| 3,898,172 A | 8/1975 | Reif et al. |
| 4,034,609 A | 7/1977 | Fuller |
| 4,050,307 A | 9/1977 | McMullen et al. |
| 4,098,120 A | 7/1978 | Manske |
| 4,130,012 A * | 12/1978 | Lockerby et al. ................. 73/73 |
| 4,150,570 A | 4/1979 | Fuller |
| 4,231,370 A * | 11/1980 | Mroz et al. ..................... 604/361 |
| 4,681,576 A * | 7/1987 | Colon et al. ................... 604/361 |
| 4,743,238 A * | 5/1988 | Colon et al. ................... 604/361 |
| 4,793,180 A | 12/1988 | Stewart et al. |
| 4,854,160 A | 8/1989 | Glatt |
| 4,895,567 A * | 1/1990 | Colon et al. ................... 604/361 |
| 6,698,378 B1 | 3/2004 | Dick et al. |
| 6,815,207 B2 * | 11/2004 | Yabuki et al. ....................... 436/2 |
| 6,877,457 B1 | 4/2005 | Dick et al. |
| 7,744,997 B2 * | 6/2010 | Birkholz et al. ............... 428/354 |
| 2003/0064190 A1 * | 4/2003 | Carte et al. ................... 428/40.1 |
| 2004/0138633 A1 * | 7/2004 | Mishima et al. ............... 604/361 |
| 2005/0106735 A1 | 5/2005 | Song et al. |
| 2009/0013760 A1 * | 1/2009 | Chiba et al. ................... 73/29.04 |
| 2009/0171307 A1 * | 7/2009 | Chang et al. ................... 604/361 |
| 2009/0311140 A1 * | 12/2009 | Yamakawa ......................... 422/55 |
| 2010/0162940 A1 * | 7/2010 | Hill et al. ......................... 116/206 |
| 2010/0264369 A1 * | 10/2010 | Zhang ....................... 252/301.35 |

FOREIGN PATENT DOCUMENTS

| | | |
|---|---|---|
| DE | 120293 | 6/1976 |
| EP | 1705484 | 9/2006 |
| JP | 58216936 A | 12/1983 |
| JP | 59157565 | 9/1984 |
| JP | 61144570 | 7/1986 |
| JP | 2007198828 | 8/2007 |
| WO | 0109601 | 2/2001 |
| WO | 03015060 A2 | 2/2003 |
| WO | 03054528 | 7/2003 |
| WO | 2009015873 | 2/2009 |

OTHER PUBLICATIONS

Extended European Search Report with respect to Application No. 10194491.6-2204, dated May 19, 2011.
Military Specification MIL-I-8835A, Mar. 10, 1959.

* cited by examiner

*Primary Examiner* — Lisa Caputo
*Assistant Examiner* — Punam Roy
(74) *Attorney, Agent, or Firm* — Scoot R. Cox

(57) ABSTRACT

The present invention provides an indicator material suitable for detecting relative humidity exceeding a specific limit value and/or liquid water comprising (a) a first fibrous sheet containing an indicator composition which comprises a water-soluble dye and, optionally, a deliquescent salt, in finely divided form, and (b) a second fibrous sheet laminated to one surface of said first fibrous sheet by means of a hot-melt adhesive that does not cover the entire surfaces laminated to each other such that permeation of an aqueous solution from said first fibrous sheet to said second fibrous sheet is allowed. The invention also provides an indicator device comprising said indicator material on a carrier and a process for the manufacture of said indicator material and said indicator device.

11 Claims, No Drawings

INDICATOR MATERIAL AND INDICATOR DEVICE COMPRISING SAID INDICATOR MATERIAL

TECHNICAL FIELD

The present invention relates to an indicator material for the detection of relative humidity exceeding a specific limit value and/or liquid water, to an indicator device comprising said indicator material, to a process for the manufacture of said indicator material and to a process for preparing said indicator device comprising said indicator material.

BACKGROUND

Many goods of modern life are sensitive to moisture and, therefore, exposure to atmosphere having a relative humidity exceeding a specific limit value when these goods are shipped or stored should be avoided. For instance, electronic components can be damaged by exposure to an atmosphere having a relative humidity exceeding a specific limit value, even when the limit value is low and the exposure is only for short period of time.

In order to ensure that quality of such goods is not deteriorated during shipping or storing, it is generally desirable to monitor the relative humidity of the atmosphere to which the goods are exposed.

For this purpose, humidity indicators have been developed. There are generally two types of humidity indicators. One of these humidity indicators reversibly changes colour upon exposure to atmosphere having a specific level of relative humidity. Such reversible humidity indicators typically utilize cobalt chloride as the humidity indicator material impregnated on blotting paper. Military specification MIL-I-8835A describes the details of construction of such indicators and performance requirements. The indicators change colour when exposed to atmosphere having a relative humidity exceeding a limit value and return to its original colour when the relative humidity of the surrounding atmosphere drops below that limit value. Reversible humidity indicators are used to indicate the current condition of a desiccant and/or the current humidity level within the storage container.

The second type of humidity indicator is an irreversible humidity indicator. These indicators are designed to detect whether relative humidity of surrounding atmosphere has exceeded a limit value and provide a visual indication of whether goods stored under said atmosphere have thus been undesirably exposed to atmosphere having a relative humidity exceeding that limit value during any period of the storage time. The irreversible humidity indicator can therefore provide an indication of whether the relative humidity of the atmosphere reached or exceeded the limit value even for limited periods of time, i.e. even if the relative humidity has subsequently dropped below that limit value, for instance when the storage conditions are checked at a later time.

Relative humidity is defined according to the following equation:

$$RH = c(H_2O)/c^{sat}(H_2O)$$

where $c(H_2O)$ is the observed content of water vapour, and $c^{sat}(H_2O)$ is the content of water vapour at saturation.

If the content of water vapour exceeds saturation, condensation occurs, i.e. liquid water is formed by condensation.

The content of water vapour at saturation is dependent on temperature. The content of water vapour at saturation is the higher, the higher the temperature is, i.e. warm air can take up more water vapour before condensation occurs.

This implies that large changes in relative humidity can occur, in particular when the temperature, at which goods are stored, changes while the content of humidity in the surrounding atmosphere remains constant. If the atmosphere at which the goods are stored has a high content of water vapour and the storage temperature drops, condensation can thus occur. This implies the risk that the stored goods can come into contact with liquid water which usually is highly detrimental.

Under these conditions, a reversible humidity indicator might fail to indicate the temporary presence of high humidity within a storage container even though such high humidity may be sufficient to cause damage to the components present in the storage container.

To maintain the relative humidity of the atmosphere consistently low, shipping containers and long term storage containers usually contain desiccant materials. These desiccant materials remove moisture from the atmosphere up to a predetermined level. The containers are periodically opened to recharge or replace the desiccant materials placed within the container and/or to check the level of relative humidity in the storage container. After replacing the desiccant material, the container is again sealed. In order to determine the relative humidity levels in these storage containers has ever reached or exceeded certain critical levels, irreversible humidity indicators are also often placed within the containers with the desiccant materials. These irreversible humidity indicators can be reviewed at the same time at which the desiccant material is being checked to determine whether a detrimental relative humidity level has ever been reached or exceeded in the shipping container.

One of the first irreversible humidity indicator devices was disclosed in U.S. Pat. No. 2,214,354, which disclosed the use of calcium chloride.

A series of relative humidity indicators, each utilizing a different deliquescent salt, are disclosed in a series of patents including U.S. Pat. Nos. 2,460,065, 2,460,066, 2,460,067, 2,460,068, 2,460,069, 2,460,070, 2,460,071, 2,460,072, 2,460,073, 2,460,074, 2,526,938, 2,580,737, 2,627,505, EP 1 200 819 A0 (also published as WO 01/09601 A1), US 2005/0106735 A1, JP 2007-198828 A and EP 1 705 484 A1.

Some indicator devices are capable of showing different relative humidity levels on the same devices by use of a series of different deliquescent agents that change colour at varying humidity levels, as disclosed in U.S. Pat. No. 2,249,867.

Humidity indicator sheets and devices which contain deliquescent salts and dyes have commonly been used to detect the relative humidity level present within storage containers. See for example, U.S. Pat. Nos. 2,249,867, 4,034,609, 4,150,570, and 4,854,160. Button-type humidity indicators or "plug" humidity indicators are also sometimes used with packaging material and are disclosed, for example, by U.S. Pat. Nos. 2,716,338, 3,084,658, and 4,050,307. Another device for monitoring humidity levels, particularly in poured cement, is disclosed in U.S. Pat. No. 3,680,364.

Another type of irreversible humidity detector is disclosed in U.S. Pat. No. 3,898,172, wherein a deliquescent salt in combination with a dye is disposed on a moisture-impervious, fused substrate. Claimed is a humidity indicator that works between 6% and 20% relative humidity at ambient temperature.

U.S. Pat. Nos. 6,877,457 B1 and 6,698,378 describe an irreversible humidity indicator device comprising several layers and a deliquescent material contained within holes of a carrier member. A coloured absorbent sheet is attached to the back side of the carrier member. A transparent cover sheet is attached to the front side. When the indicator device is exposed to atmosphere having a suitable specific relative humidity, the deliquescent material liquefies and the thus formed solution is absorbed by the coloured absorbent sheet. Thus, the coloured absorbent sheet becomes visible through the transparent cover sheet. Irreversible humidity indicator devices of this type have the disadvantage that their manufacture is relatively complex, in particular because it is necessary to completely fill the holes with the deliquescent material.

A similar irreversible humidity indicator device is disclosed in U.S. Pat. No. 4,793,180. A deliquescent agent (such as an inorganic salt) that is coated with a water-soluble dye is arranged within a recess formed in a porous plastic carrier and covered with a sheet of absorbent material such as a blotting paper. When the deliquescent agent interacts with moist atmosphere, it eventually liquefies and forms a solution coloured due to the presence of the water-soluble dye. This solution is absorbed by the blotting paper that is thus stained and irreversibly indicates that the device was exposed to moist atmosphere. Similar to the humidity indicator device described in the preceding section, the manufacture of humidity indicator devices of this type is relatively complex.

Another irreversible humidity indicator was suggested in JP 61-144570 based on a filter paper impregnated with a deliquescent chemical and a colour forming reagent.

A sensor for indicating a cumulative time period of presence of an ambient relative humidity was disclosed in WO 03/054528 A1, comprising an indicator and a carrier, with the indicator located on one or more limited portions of the carrier. The carrier is a hygroscopic material, allowing a migration of the (colour) indicator in the carrier.

In Patent WO 2009/015873 A2 another cumulative moisture sensor is described, comprising a matrix of a hygroscopic material, a first and second reagent that react only in the presence of water.

In DD 120293, another irreversible humidity indicator device system has been suggested on the basis of an absorbent paper, immersed with saturated salt solution and the dry paper dyed on one side. A paper prepared according to this suggestion cannot be handled, because the salt crystallizes on the surfaces and will exfoliate as soon as moved or touched. Furthermore, it cannot be dyed due to exfoliation.

Yet another humidity indicator device system for the testing of water activity of food was suggested in JP 59-157565 A based on a moisture absorber layer, a moisture permeable sheet and a filter paper impregnated with a dye that discolours with water, e.g. a cobalt salt.

U.S. Pat. No. 4,098,120 disclosed a humidity indicating method and device suitable for indicating a humidity-time history. The invention is based on a deliquescent salt, a liquid absorbing wick, and an indicator means. A solution of a deliquescent salt and an indicator dye is absorbed onto a filter paper reservoir, dried, and the wick, prepared of filter paper as well, is brought and held into contact with the filter paper reservoir by enveloping the wick and the filter paper reservoir with a transparent cover.

It is crucial for the reliable and reproducible indication of elevated relative humidity that an intimate contact between the reservoir and the wick is established and maintained in a reliable and reproducible manner in order to avoid that wicking of the solution of the deliquescent salt is influenced. It was found that the intimate contact between a reservoir and a wick necessary for a reliable and reproducible indication of humidity can not be ensured in the device disclosed in U.S. Pat. No. 4,098,120. Furthermore, it was found that the manufacture of said device is relatively complex. Likewise, it is scarcely possible to reduce the dimensions of the device to such an extent that it becomes possible to employ it in miniature applications such as on individual diagnostic test strips, for instance.

The humidity indicator devices known from the prior art as summarized hereinabove have the disadvantage that their manufacture is relatively complex and therefore requires manual work and/or that the indication of humidity is prone to give erroneous results and hence not reliable. Furthermore, the humidity indicator devices known from the prior art are not suitable for miniature applications as their dimensions can not be sufficiently reduced.

It is a first object of the present invention to provide an indicator material suitable for detecting relative humidity exceeding a specific limit value and/or liquid water in a reliable manner and which can be manufactured in a straightforward manner. The indicator material should be suitable for detecting the temporary presence of liquid water and/or elevated relative humidity, i.e. a positive detection result should be obtained, even if at the time of reading the indicator material any water has evaporated and the relative humidity has dropped below the specific limit value.

The indication of relative humidity exceeding a specific limit value and/or liquid water should be suitable for automatic detection, i.e. that it does not require visual inspection by personnel.

It is another object of the present invention to provide an indicator device comprising an indicator material according to the first object of the present invention.

It is a further object of the present invention to provide a process for the manufacture of an indicator material according to the first object of the present invention. This process should be suitable for automatic production in large quantities.

It is a yet further object of the present invention to provide a process for the manufacture of an indicator device comprising the indicator material that is suitable for mass production by automatic manufacture. This process should be suitable for automatic production in large quantities.

DESCRIPTION OF THE INVENTION

Surprisingly, as the first aspect of the present invention, it was found that the first object can be achieved by providing an indicator material comprising
(a) a first fibrous sheet,
(b) a second fibrous sheet laminated to one surface of said first fibrous sheet by means of a hot-melt adhesive that does not cover the entire surfaces laminated to each other such that permeation of an aqueous solution from said first fibrous sheet to said second fibrous sheet is allowed,
(c) an indicator composition which comprises (c1) a water-soluble dye and, optionally, (c2) a deliquescent salt and is contained in said first fibrous sheet in finely divided form.

As the second aspect of the present invention, it was found that an indicator device comprising said indicator material can be made available by providing the indicator material according to the abovementioned first aspect of the present invention on a carrier.

As the third aspect of the present invention, it was found that a process for the manufacture of an indicator material according to the first aspect of the present invention comprises
(i) providing a hot-melt adhesive on portions of one surface of a first fibrous sheet in such manner that a regular or irregular geometric pattern of hot-melt adhesive is formed on the surface of the first fibrous sheet such that the surface can be laminated to a second fibrous sheet and not the entire surface to be laminated is covered with the hot-melt adhesive, (ii) impregnating the first fibrous sheet with a solution of an indicator composition which comprises (c1) a water-soluble dye and, optionally, (c2) a deliquescent salt, (iii) removing the solvent from the impregnated first fibrous sheet, (iv) laminating a second fibrous sheet to the first fibrous sheet by heating the hot-melt adhesive provided on the first fibrous sheet to a temperature sufficient to adhere to the second fibrous sheet, pressing the second fibrous sheet onto the hot-melt adhesive, and cooling the hot-melt adhesive.

As the fourth aspect of the present invention, it was found that a process for the manufacture of the indicator device comprising the indicator material comprises the steps of (i) providing an indicator material as defined in the first aspect of the present invention, (ii) imparting a specific geometric shape to the indicator material, (iii) arranging said at least one indicator material on a carrier in such a manner that the surface of the second fibrous sheet of each of the at least one indicator material can be observed, and that the indicator material can be accessed by any liquid water and/or elevated relative humidity that is present in the surrounding of the indicator device.

Hereinafter, the invention will be described in more detail.

In this description, the term "elevated relative humidity" will be used in order to refer to relative humidity exceeding a specific limit value, i.e. higher than a specific limit value. Thus, the term "atmosphere having an elevated relative humidity" means that the relative humidity of the atmosphere is higher than a specific limit value.

By means of the indicator material according to the present invention, the detection of elevated relative humidity and the detection of liquid water both is achieved by the formation of an aqueous solution of the water-soluble dye (c1) contained in the indicator composition (c) that is finely distributed in the first fibrous sheet and subsequent absorption of the solution (which appears coloured to the human eye when irradiated with light from the spectral region visible to the human eye or from the ultraviolet spectral region due the presence of the dissolved dye) by the second fibrous sheet that is laminated to one of the surfaces of the first fibrous sheet by means of a hot-melt adhesive. As a result, the second fibrous sheet is stained by the coloured solution. Hence, the coloured aqueous solution formed in the first fibrous sheet is wicked into the second fibrous sheet. Staining becomes visible when the coloured solution has migrated from the surface of the second fibrous sheet that is laminated to the first fibrous sheet to the opposite surface of the second fibrous sheet (which is the observable surface).

Thus, if the indicator composition (c) contains the water-soluble dye (c1) as the only component, the staining of the second fibrous sheet allows to detect that liquid water has been in contact with the first fibrous sheet and the indicator composition (c) (i.e. the water-soluble dye (c1)) finely distributed therein and dissolved the water-soluble dye (c1) at least partially.

If the indicator composition (c) contains the water-soluble dye (c1) and the deliquescent salt (c2), the staining of the second fibrous sheet likewise allows detecting that liquid water has been in contact with the first fibrous sheet and the indicator composition (c) finely distributed therein and dissolved the water-soluble dye (c1) at least partially.

In addition, it is possible to detect that the relative humidity of the surrounding atmosphere has reached or exceeded the limit value at which deliquescence of the deliquescent salt (c2) takes place, thus forming a liquid solution of the deliquescent salt. The thus formed liquid solution also dissolves at least a part of the water-soluble dye (c1) such that a coloured solution is formed. The coloured solution is absorbed by the second fibrous sheet that is laminated to one of the surfaces of the first fibrous sheet and, as a result, the second fibrous sheet is stained by the coloured solution.

Irrespective of whether the indicator composition (c) contains said water-soluble dye (c1) only or contains said water-soluble dye and said deliquescent salt (c2), the staining of the second fibrous sheet is maintained even if said elevated relative humidity and/or the liquid water was temporarily present only and subsequent to the staining of the second fibrous sheet any water evaporated and the relative humidity dropped below the specific limit value, for instance. Thus, the staining is not reversible.

As a result, an indicator material is provided that is suitable for detecting elevated relative humidity and/or liquid water in an irreversible manner.

Therefore, the indicator material according to the first aspect of the present invention can be used for the manufacture of an indicator device showing the presence of liquid water and/or elevated relative humidity in an irreversible manner.

In the following, the components of the indicator material and the indicator device according to the present invention will be explained in more detail.

(a) First Fibrous Sheet

The first fibrous sheet of the indicator material of the present invention is composed of fibres and is non-woven, woven or knitted, i.e. the individual fibres are entangled in a regular (in the case of a woven or knitted sheet) or irregular manner (in the case of a non-woven sheet). Due to the entanglement of fibres, voids are present between the fibres which can be accessed from outside. The voids present between the fibres can hence be regarded as representing capillaries having an irregular shape. Due to the presence of such voids, the sheet can accommodate the indicator composition in finely divided form, namely in the voids formed between the individual fibres.

When the fibrous sheet is non-woven, the fibres or filaments are entangled mechanically, thermally or chemically.

The material of the fibres can be selected from a natural polymer such as cotton, wool, cellulose, hemp, flax or a synthetic polymer such as polyolefins, polyamides, polyesters, polyethers, polylactic acids and combinations thereof. The synthetic polymer can be a homopolymer or a copolymer. The material of the fibres can consist of a single material or two or more materials. Furthermore, fibres of different materials can be combined in the first fibrous sheet. Non-woven fabrics manufactured from polyester fibres have been found to be particularly suitable for being used as the first fibrous sheet of the present invention.

The voids present between the fibres generate capillary forces such that the fibrous sheet has the capability of wicking a solution of the indicator composition such that the solution of indicator composition is uniformly distributed over the entire sheet. As the solution of the indicator composition is coloured due to the present of the water-soluble dye (c1), a uniform distribution implies a uniform colouring of the sheet which can be observed by visual inspection.

In order to impart the capability of being laminated to the second fibrous sheet (b) of the indicator material according to the present invention, a hot-melt adhesive is present on one surface of the first fibrous sheet. The hot-melt adhesive is arranged on the surface of the fibrous sheet in a geometrically regular or arbitrary pattern of dots or lines. A pattern of dots can be formed by applying the hot-melt adhesive to the surface of the fibrous sheet in molten state in the form of droplets and solidifying the hot-melt adhesive by cooling. A pattern of lines can be formed by applying the hot-melt adhesive in molten state in the form of a thin stream emitted from a nozzle. A pattern of dots and/or lines can be formed by techniques such as screen printing. The specific geometric arrangement of the droplets or lines on the surface of the fibrous sheet is not particularly limited as long as the hot-melt adhesive is distributed on the surface of the fibrous sheet in such a manner that the second fibrous sheet can be laminated in a uniform manner to the first fibrous sheet. An exemplary line pattern is a grid-like pattern. In a pattern of dots, the dots can have a diameter of 0.8 mm, for instance.

However, in order to allow that an aqueous solution of the indicator composition formed in the first fibrous sheet can be absorbed by the second fibrous sheet that is laminated to the first fibrous sheet, not the entire surface of the first fibrous sheet is covered with the hot-melt adhesive.

For this purpose, preferably 5-40% of the area of the surface of the first fibrous sheet that is to be laminated with the second fibrous sheet is covered with the hot-melt adhesive. In order to ensure the contact between the first and the second sheet required for the absorption of any coloured solution formed in the first fibrous sheet and in order to avoid partial delamination of the sheets, it is preferred that not less than 5% of the area of the surface of the first fibrous sheet that is to be laminated with the second fibrous sheet is covered with the hot-melt adhesive.

The hot-melt adhesive can spread on the surface of the first and the second fibrous sheet during laminating when the hot-melt adhesive is in a softened state and pressure is applied in order to adhere the fibrous sheets. In order to avoid that the hot-melt adhesive acts as a barrier layer formed between the first and the second fibrous sheet and impairs the permeation and absorption of any coloured solution formed in the first fibrous sheet, it is preferred that not more than 40% of the area of the surface of the first fibrous sheet that is to be laminated with the second fibrous sheet is covered with the hot-melt adhesive.

The term "hot-melt adhesive" commonly relates to a polymer being solid at room temperature and having a relatively low softening or melting point, for instance a polyolefin having relatively low molecular weight. The adhesive activity is achieved by heating the polymer to a temperature above room temperature such that it softens or melts, adhering it to a substrate and solidifying by cooling. A polymer that is used as hot-melt adhesive is provided in compact form, i.e. voids are inherently not present in the polymer, in order to prevent that the adhesion is weakened.

Hence, the hot-melt adhesive on the surface of the first fibrous sheet inherently does not contain voids that can generate capillary forces. Furthermore, since hot-melt adhesives usually are hydrophobic polymers such as polyolefins, the hot-melt adhesive present on the surface of the first fibrous sheet is not covered with the indicator composition when the indicator composition is applied to the first fibrous sheet and, as a result, after drying the indicator composition does not cover the hot-melt adhesive. The hot-melt adhesive thus remains accessible for being brought into contact with the second fibrous sheet during the lamination step.

The hot-melt adhesive is activated by heating, i.e. it is molten or softened, i.e. brought to a state of relatively low viscosity in which it adheres to materials with which it is brought into contact. In order to be suitable for being used in the present invention, the hot-melt adhesive can be activated by heating to a temperature that is compatible with the material of the first and second fibrous sheet and the indicator composition, i.e. the fibres of the first and second fibrous sheet remain intact and the water-soluble dye and the deliquescent salt are not decomposed. For this reason, the hot-melt adhesive suitable for being used in the present invention can be activated by being heated to a temperature of 90-210° C., preferably 110-160° C.

Preferred non-woven fabrics suitable for being used in the present invention are made from polyester by a dry-laid process, are thermally bonded and show an area density of 40-60 g/m$^3$. As the hot-melt adhesive, polyamide can be utilized in a dot matrix in an area density of 20-40 g/m$^2$.

(b) Second Fibrous Sheet

Similar to the first fibrous sheet of the indicator material of the present invention, the second fibrous sheet is composed of fibres and is non-woven, woven or knitted, i.e. the individual fibres are entangled in a regular (in the case of a woven or knitted sheet) or irregular manner (in the case of a non-woven sheet). Due to the entanglement of fibres, voids are present between the fibres which can be accessed from outside.

The voids present between the fibres can be regarded as representing capillaries which generate capillary forces. By means of such capillary forces the fibrous sheet has the capability of wicking an aqueous solution of the indicator composition such that the solution of indicator composition is uniformly distributed over the entire sheet. As the solution of the indicator composition is coloured due to the presence of the water-soluble dye (c1), a uniform distribution implies a uniform colouring of the sheet which can be observed by visual inspection (under UV irradiation if the water-soluble dye (c1) is a fluorescent dye).

When the fibrous sheet is non-woven, the fibres or filaments are entangled mechanically, thermally or chemically.

The material of the fibres can be selected from a natural polymer such as cotton, wool, cellulose, hemp, flax or a synthetic polymer such as polyolefins, polyamides, polyesters, polyethers, polylactic acids and combinations thereof. The synthetic polymer can be a homopolymer or a copolymer. The material of the fibres can consist of a single material or two or more materials. Furthermore, fibres of different materials can be combined in the first fibrous sheet. Non-woven fabrics manufactured from polyester fibres have been found to be particularly suitable for being used as the first fibrous sheet of the present invention.

Paper is formed from wet-laid cellulose fibres and can be regarded as being a non-woven. It was found that blotting papers and filter papers are particularly suitable as the second fibrous sheet of the indicator material.

As set out hereinabove, staining of the second fibrous sheet becomes visible when the coloured solution formed in the first fibrous sheet has migrated from the surface of the second fibrous sheet that is laminated to the first fibrous sheet to the opposite surface (which is the observable surface).

Generally, migration of the coloured solution to the observable surface of the second fibrous sheet takes longer when the thickness of the second fibrous sheet is higher.

In order to allow detection of staining of the second fibrous sheet, the second fibrous sheet has an appropriate colour, i.e. a colour that does not impair detection of the colour impression resulting from the presence of the water-soluble dye (c1).

(c) Indicator Composition

The indicator composition that is finely distributed in the first fibrous sheet comprises a water-soluble dye (c1) and, as an optional component, a deliquescent salt (c2).

The indicator composition comprises a water-soluble dye (c1) if it has to be suitable for the detection of liquid water only, but not for the detection of gaseous water, i.e. for the detection of elevated relative humidity of the surrounding atmosphere. In this case, the indicator composition can comprise the water-soluble dye (c1) in an amount of 50 to 100% by weight, preferably in an amount of 70 to 100% by weight, more preferably in an amount of 85 to 100% by weight, yet more preferably in an amount of 90 to 100% by weight, still more preferably in an amount of 95 to 100% by weight, relative to the total weight of the indicator composition. Most preferably, the indicator composition comprises the water-soluble dye (c1) in an amount of 100% by weight relative to the total weight of the indicator composition, i.e. the indicator composition exclusively consists of the water-soluble dye (c1).

In contrast, if the indicator composition is to be suitable for the detection of gaseous water, i.e. for the detection of elevated relative humidity, the indicator composition has to comprise both a water-soluble dye (c1) and a deliquescent salt (c2).

In this case, the sum of the amount of water-soluble dye (c1) and the amount of deliquescent salt (c2) can represent 50 to 100% by weight of the indicator composition. In a preferred embodiment, the sum of the amount of water-soluble dye (c1) and the amount of deliquescent salt (c2) represents 70 to 100% by weight of the indicator composition. More preferably, the sum of the amount of water-soluble dye (c1) and the amount of deliquescent salt (c2) represents 85 to 100% by weight, yet more preferably 90 to 100% by weight, still more preferably 95 to 100% by weight, relative to the total weight of the indicator composition. Most preferably, the sum of the amount of water-soluble dye (c1) and the amount of deliquescent salt (c2) represents 100% by weight of the indicator composition, relative to the total weight of the indicator composition, i.e. the indicator composition exclusively consists of the water-soluble dye (c1) and the deliquescent salt (c2).

If the indicator composition comprises both a water-soluble dye (c1) and a deliquescent salt (c2), it can contain a combination of two or more deliquescent salts. Usually, the indicator composition contains a single deliquescent salt only.

The amount of the water-soluble dye (c1) can be in the range of 0.01 to 30% by weight, preferably in the range of 0.02 to 20% by weight, more preferably in the range of from 0.03 to 10% by weight and most preferably in the range of from 0.04 to 8% by weight, relative to the amount of the deliquescent salt (c2).

(c1) Water-Soluble Dye

The term "dye" relates to a chemical compound or to a combination of chemical compounds which is capable of absorbing electromagnetic radiation in the visible spectrum, i.e. in the range of wavelength perceptible with the human eye (about 380-790 nm, also abbreviated as "VIS"), or to a fluorescent dye. The term "fluorescent dye" as used in the context of the present invention is capable of absorbing electromagnetic radiation in the spectral range adjacent to the lower limit of the wavelength of the visible spectrum, commonly referred to as ultraviolet spectrum (about 200-380 nm, also abbreviated as "UV"), but not to a significant extent in the VIS spectrum, i.e. no strong colour impression is perceivable with the human eye in the absence of UV irradiation. When a fluorescent dye is irradiated with radiation having a suitable wavelength in the UV spectrum, it emits radiation in the visible spectrum which can be perceived with the human eye as being coloured.

A fluorescent dye having this property can not be perceived with the human eye, when it is not irradiated with radiation having a wavelength in the UV spectrum, i.e. it appears as being "colourless".

The use of a fluorescent dye in the present invention as the water-soluble dye (c1) offers the advantage that a colour can not be perceived by the human eye in the absence of UV radiation having a suitable wavelength such that stains caused by an aqueous solution of the dye accidentally leaving the indicator material of the present invention into the surroundings (possibly due to excessive exposure to liquid water) are not visible under daylight or artificial illumination commonly used for lighting rooms and areas intended for sojourn of humans.

The dye contained in the indicator composition has to be soluble in water, i.e. the amount of dye soluble in water at room temperature has to be so high that a solution is obtained that is intensely coloured. If the amount soluble in water is too low, detection of staining of the second fibrous sheet can be difficult or impossible such that a reliable detection of elevated relative humidity and/or liquid water is impaired.

As exemplary dyes that are suitable for being used in the present invention because they have a sufficiently high solubility in water and give intense colouring, dyes commonly used for food colouring can be mentioned.

Such dyes can be synthetic dyes (i.e. man-made compounds) or natural products.

Such dyes have usually been approved by competent authorities for use in foods, beverages, drugs and cosmetics and have been assigned corresponding codes as a simple reference. Thus, in the United States, such dyes usually have been assigned FD&C numbers (such as FD&C Blue No. 1, also known as Brilliant Blue FCF or Acid Blue 9, an organic dye having a triphenylmethane scaffold). In the European Union, such dyes usually have been assigned E numbers (such as E133, which denotes Brilliant Blue FCF as well).

Exemplary dyes suitable for being used in the present invention are listed in the following, wherein synonyms and, where applicable, E numbers and FD&C numbers are indicated in parentheses.

Brilliant Blue FCF (Acid Blue 9, E133, FD&C Blue No. 1)
Riboflavine (E101)
Patentblue VF sodium salt (Acid Blue 1)
Acid Fuchsine (Acid Magenta, Acid Violet 19)
Acid Blue 40 (Alizarin direct blue A2G)
Basic Blue 9 (Methylene blue)
Acid Violet 6
Acid Violet 12
Acid Yellow 23
Basic green 4 (Malachite green)
Litmus
Cyanidine
Xylenol blue
Neutral red (Basic red 5)
Thymol blue
Alizarin
Alkaline blue As an example of a fluorescent dye suitable for being used in the present invention, quinine can be mentioned, which absorbs radiation having a wavelength of about 346 nm and emits radiation at a wavelength of about 451 nm, thus resulting in the perception of a bluish or greenish colour. In contrast, in a diluted aqueous solution, it does not absorb a significant amount of radiation from the VIS spectrum and the solution thus is perceived as being transparent or colourless.

As other examples of fluorescent dyes uranine (fluorescein sodium salt), fraxine, aesculine and protoporphyrin IX can be mentioned.

(c2) Deliquescent Salt

The deliquescent salt (c2) represents an optional component of the indicator composition as its presence is not required if the indicator material is intended for the detection of liquid water only. In contrast, if the indicator material is intended for the detection of gaseous water only or for the detection of both gaseous and liquid water, the deliquescent salt (c2) has to be present in the indicator composition.

The term "deliquescent" relates to the property of a salt to absorb moisture from the surrounding atmosphere, usually air, to such an extent that the salt eventually dissolves in the absorbed water and forms a solution. Various salts have this property and hence deliquesce when exposed to atmosphere having a specific minimum moisture content.

As indicated hereinabove, relative humidity is defined as the ratio of the observed content of water vapour to the content of water vapour at saturation.

Relative humidity is usually expressed as a percentage.

Absorption and desorption is governed by a dynamic equilibrium. Thus, only when the relative humidity of atmosphere surrounding a specific deliquescent salt has reached a specific minimum level, the salt absorbs moisture in an amount sufficient to form a saturated solution, i.e. a solution containing the maximum amount of salt soluble in water at the specific temperature. The formed saturated solution and the surrounding atmosphere having said specific minimum relative humidity are in a state of equilibrium, i.e. the rate of moisture absorption from the surrounding atmosphere by the saturated solution is equal to the rate of desorption of moisture from the saturated solution to the surrounding atmosphere.

This implies that the relative humidity that is established over a saturated solution of specific salt at a specific temperature as a result of this equilibrium is equal to the abovementioned minimum level of relative humidity. Thus, lists of deliquescent salts suitable for being used in the indicator composition can be found in the prior art such as in "Handbook of Chemistry and Physics", D. R. Lide (ed.), 73rd edition 1992-1993, CRC Press, Boca Raton, USA, page 15-20 and L. B. Rockland, Anal. Chem. 32, (1960), pages 1375-1376, in which the data shown in the following table have been disclosed, indicating the minimum level of relative humidity at 25° C. (unless indicated otherwise) at which deliquescence occurs.

Of course, the deliquescent salt has to be compatible with the water-soluble dye and the material of the first and second fibrous sheet. In this respect, in particular the deliquescent salt is selected in such a manner that the oxidizing and reducing power does not deteriorate the water-soluble dye. Likewise, the deliquescent salt is selected such that any acidic or basic properties do not affect the colour of the dye.

Thus, salts containing anions such as permanganate, chromate, dichromate, nitrate, chlorate, perchlorate, hypochlorite etc. are not preferred as the deliquescent salt used in the present invention.

| Salt | deliquescent at 25° C./RH [%] |
|---|---|
| $LiBr \cdot 2H_2O$ | 6 |
| $ZnBr_2 \cdot 2H_2O$ | 8 |
| $LiCl \cdot H_2O$ | 11 |
| $CaBr_2 \cdot 6H_2O$ | 16 |

-continued

| Salt | deliquescent at 25° C./RH [%] |
|---|---|
| $LiI \cdot 3H_2O$ | 18 |
| potassium acetate | 23 |
| $CaCl_2 \cdot 6H_2O$ | 29 |
| $MgCl_2 \cdot 6H_2O$ | 33 |
| $NaI \cdot 2H_2O$ | 38 |
| $K_2CO_3$ | 43 |
| $NaBr \cdot 2H_2O$ | 58 |
| KI | 69 |
| NaCl | 75 |
| sodium acetate | 76 |
| $NH_4Cl$ | 79 |
| KBr | 81 |
| $(NH_4)_2SO_4$ | 81 |
| KCl | 84 |
| $ZnSO_4 \cdot 7H_2O$ | 90 (20° C.) |
| CsI | 91 |
| $K_2SO_4$ | 97 |

The deliquescent salt is generally selected depending on the limit value of the relative humidity that is to be detected.

For instance, if the indicator material according to the present invention is to be suitable for the detection of a relative humidity of 70% or higher at 25° C., potassium iodide (deliquescent at a relative humidity of 69% at 25° C.) could be selected from the abovementioned list.

If the indicator material according to the present invention is to be suitable for the detection of a relative humidity of 30% or higher at 25° C., calcium chloride hexahydrate (deliquescent at a relative humidity of 29% at 25° C.) could be selected from the abovementioned list.

Thus, an indicator composition containing Brilliant Blue FCF as the water-soluble dye (c1) and potassium iodide as the deliquescent salt (c2) can be used in an indicator material of the present invention suitable for detecting a relative humidity of 70% or higher at 25° C. by causing a blue staining of the second fibrous sheet (b).

The Indicator Material

The indicator material of the present invention comprises a first fibrous sheet, a second fibrous sheet that is laminated to one surface of the fist fibrous sheet and an indicator composition that is present in finely distributed form.

Exemplary combinations of the first fibrous sheet and the second fibrous sheet that have been found to be particularly suitable for the wicking of an aqueous solution from the first fibrous sheet into the second fibrous sheet are combinations in which the first fibrous sheet is a non-woven manufactured from polyester fibres and the second fibrous sheet is a non-woven manufactured from cotton or cellulose fibres such as a filter paper or a blotting paper.

The indicator material according to the present invention is conveniently stored under a dry atmosphere until it is further processed.

Indicator Device Comprising Said Indicator Material

The indicator device according to the present invention comprises at least one indicator material described hereinabove that is arranged on a carrier in such a manner that (i) the surface of the second fibrous sheet of the indicator material (i.e. of each of the indicator materials, if more than one indicator material is present on the device) can be observed, and that (ii) the indicator material can be accessed by any liquid water and/or elevated relative humidity that is present in the surrounding of the indicator device.

The indicator material arranged on the carrier can have any conceivable geometric shape. Usually, the shape of the indicator material(s) is circular or regular-polygonal (such as rectangular, for instance). A specific geometric shape can be imparted by cutting using a blade or by die cutting, for instance.

While it is usually sufficient to arrange one indicator material on the carrier, it can be advantageous to arrange the same indicator material in several areas on the carrier, for instance if it is desired that to provide an indicator device allowing to counter-check the reading of the indicator material in one area with the reading of the indicator material in another area in order to avoid erroneous readings.

It is also possible to arrange several different indicator materials according to the present invention on the carrier, wherein each indicator material contains an indicator composition suitable for detecting a different value of elevated relative humidity (by the presence of a different deliquescent salt in the indicator composition).

In order to provide for a comparison of a positive and negative detection result, i.e. of a stained and unstained second fibrous sheet of the indicator material, the second fibrous sheet used in the indicator material can be arranged on the carrier as a blank sample. Thus, readability of the indicator device can be further improved and erroneous readings can be avoided.

This applies in particular to automatic detection of the results by reading the indicator device using a spectroscopic device. Automatic reading can be carried out by measuring the intensity of the electromagnetic radiation reflected (in the case where a water-soluble dye (c1) absorbing radiation in the VIS spectrum is present in the indicator material) or emitted (in the case where a fluorescent water-soluble dye (c1), i.e. absorbing radiation in the UV spectrum and emitting radiation in the VIS spectrum, is present in the indicator material) by the indicator material using an appropriate spectroscopic device.

In this case, automatic reading is set such that the spectroscopic device reads the blank sample and separately reads the indicator material and the readings are compared by calculating a ratio of the reading of the indicator material and the blank sample. A limit value for the ratio thus calculated can be defined as a threshold in order to distinguish between positive and negative detection results.

The material of the carrier is not particularly limited and can be metal, wood, a synthetic polymeric material (plastics), paper, cardboard, glass etc. Preferably, the carrier is not transparent in order to avoid that the indicator device is erroneously read by observing the first fibrous sheet through the carrier. In this case, the indicator material will always appear coloured due to the presence of the indicator composition in the first fibrous sheet. As a consequence, a positive result will be obtained irrespective of whether the indicator device has in fact been exposed to liquid water and/or elevated relative humidity.

The carrier can have any conceivable shape. The shape will be adapted according to the requirements of the application of the indicator device. Thus, it is possible, for instance, to arrange the indicator material on one end of long strip used as the carrier. Thus, the indicator material could be brought into a position having limited accessibility only (such as narrow slits, for instance) and could be removed for reading the indicator material by using the end of the strip that is opposite to the indicator material as a handle.

The carrier can be provided with means for attaching the indicator device to an item in order to ensure that the indicator device detects whether said item has been exposed to liquid water and/or elevated relative humidity. Such means for attaching the indicator device can be an adhesive strip or spot, a strip or spot containing a permanently magnetic material (such that the indicator device can be attached to a ferromagnetic item), for instance.

The indicator device according to the present invention is conveniently stored under a dry atmosphere until it is used.

Process for the Manufacture an Indicator Material

The indicator material according to the present invention can be manufactured by a process comprising the steps of (i) providing a hot-melt adhesive on portions of one surface of a first fibrous sheet in such manner that a regular or irregular geometric pattern of hot-melt adhesive is formed on the surface of the first fibrous sheet such that the surface can be laminated to a second fibrous sheet and not the entire surface to be laminated is covered with the hot-melt adhesive, (ii) impregnating the first fibrous sheet with a solution of an indicator composition which comprises (c1) a water-soluble dye and, optionally, (c2) a deliquescent salt, (iii) removing the solvent from the impregnated first fibrous sheet, (iv) laminating a second fibrous sheet to the first fibrous sheet by heating the hot-melt adhesive provided on the first fibrous sheet to a temperature sufficient to adhere to the second fibrous sheet, pressing the second fibrous sheet onto the hot-melt adhesive, and cooling the hot-melt adhesive.

The properties of the first fibrous sheet and the hot-melt adhesive provided in step (i) have been described hereinabove with respect to the indicator material of the present invention.

The solution of the indicator composition used for impregnating should contain the water-soluble dye (c1) in an amount sufficient to achieve an intense colouring of the solution. Thus, it is ensured that an amount of water-soluble dye is incorporated into the first fibrous sheet that is sufficient to lead to intense staining of the second fibrous sheet when the presence of liquid water and/or elevated relative humidity is detected.

If the optional deliquescent salt (c2) is present in the indicator composition, i.e. if the indicator material is to be suitable for the detection of elevated relative humidity as well, the amount of the deliquescent salt present in the solution of the indicator composition should be sufficiently high in order to ensure that sufficient water is absorbed when elevated relative humidity is detected such that sufficient aqueous solution of the indicator composition is formed in the first fibrous sheet which can then be absorbed by the second fibrous sheet. For this purpose, the concentration of deliquescent salt in the solution of the indicator composition used for impregnating of the first fibrous sheet is set close to the concentration at which saturation is reached.

The solvent present in the solution of the indicator composition can be any solvent that is capable of dissolving the water-soluble dye (c1) and, if the indicator composition also contains the deliquescent salt (c2), the deliquescent salt (c2), provided that (i) the solvent does not deteriorate the material and/or the void structure of the first fibrous sheet and/or of the second fibrous sheet and/or the hot-melt adhesive and (ii) the solvent can be evaporated under conditions that do not deteriorate the material and/or the void structure of the first fibrous sheet and/or of the second fibrous sheet and/or the hot-melt adhesive.

As exemplary solvents, lower alcohols such as methanol, ethanol, propanol and isopropanol can be mentioned.

In particular, if the indicator composition contains both the water-soluble dye (c1) and the deliquescent salt (c2), the solvent usually has to be an aqueous solvent in order to be suitable for dissolving a sufficiently high amount of the deliquescent salt. The term "aqueous solvent" refers to pure water or to a homogeneous mixture of water and an organic solvent (i.e. the organic solvent completely dissolves in the water) consisting of 70% by weight to less 100% by weight of water and more than 0% by weight to 30% by weight of said organic solvent. As exemplary organic solvents methanol, ethanol, propanol and isopropanol can be mentioned.

Preferably, the solvent is pure water in order to avoid the need to evaporate volatile organic compounds (VOCs) which is critical under aspects of occupational health and safety and under ecological aspects.

The step of impregnating the first fibrous sheet can be carried out by applying a solution of the indicator composition to the first fibrous sheet and allowing the fibrous sheet to wick the solution of the indicator composition into the sheet. Applying said solution to the sheet can be carried out by any suitable method such as dipping, spraying and brushing. The solution can be applied in a single step or in two or more steps.

If the indicator composition contains both the water-soluble dye (c1) and the deliquescent salt (c2), it is also possible to apply the water-soluble dye (c1) and the deliquescent salt (c2) in separate solutions. The separate solution can contain different solvents.

Depending on the method used for impregnating, it can be advantageous to avoid that saturation of the solution is reached, i.e. to adjust the concentration to a value lower than saturation. For instance, when spraying is used for applying the solution of the indicator composition to the first fibrous sheet, undesirable crystallization of the deliquescent salt at the spraying nozzle could occur, when a saturated solution is used.

The amount of solution of the indicator composition applied to the first fibrous sheet can be as high as possible as long as dripping of the solution from the fibrous sheet is avoided in order to avoid an unnecessary loss of the indicator composition and contamination of the production site with the (intensely coloured) indicator composition.

Removing the solvent from the first fibrous sheet impregnated with the solution of the indicator composition can be carried out at room temperature or at elevated temperature in order to achieve drying in a shorter period of time. For instance, drying can be carried out at a temperature of 80° C. In any case, the temperature at which the water is removed from the impregnated first fibrous sheet should be lower than the temperature at which the hot-melt adhesive is activated. As a result, a first fibrous sheet containing the indicator composition in finely divided form is obtained.

The step of laminating the second fibrous sheet to the first fibrous sheet is carried out by heating the first fibrous sheet containing the indicator composition in finely divided form to a temperature at which the hot-melt adhesive adheres to the second fibrous sheet when the second fibrous sheet is pressed onto the surface of the first fibrous sheet on which the hot-melt adhesive is provided, pressing the second fibrous sheet onto the surface of the first fibrous sheet on which the hot-melt adhesive is provided, and cooling the hot-melt adhesive while pressing the second fibrous sheet onto the surface of the first fibrous sheet in order to bond the second fibrous sheet to the first fibrous sheet. As a result, a laminate of the second fibrous sheet and the first fibrous sheet containing the indicator composition in finely divided form is obtained which is suitable as an indicator material according to the present invention.

The step of laminating can be carried out by passing the impregnated first fibrous sheet and the second fibrous sheet through the nip between rollers that have been heated to an appropriate temperature. The nip, the temperature of the rollers and the velocity at which the sheets are passed through the nip are set in an appropriate manner in order to achieve that adequate pressure is exerted on the sheets and that the hot-melt adhesive on the surface of the first fibrous sheet is heated to a temperature sufficiently high to adhere to the surface of the second fibrous sheet. Subsequently, the laminated sheets can be passed through the nip between cooling rollers in order to solidify the hot-melt adhesive while pressure is exerted.

Process for the Manufacture of an Indicator Device

The indicator device comprising the indicator material according to the present invention can be manufactured by a process comprising the steps of (i) providing an indicator material as described hereinabove, (ii) imparting a specific geometric shape to the indicator material, (iii) arranging said at least one indicator material on a carrier in such a manner that the surface of the second fibrous sheet of each of the at least one indicator material can be observed, and that the indicator material can be accessed by any liquid water and/or elevated relative humidity that is present in the surrounding of the indicator device.

The step of imparting a specific geometric shape to the indicator material can be carried out by cutting using a blade or by die cutting, for instance. The specific geometric shape of the indicator material is not particularly limited.

The carrier is as described hereinabove with respect to the indicator device.

The indicator material is arranged on the carrier, i.e. placed on the carrier and fixed by appropriate means. The means have to allow that surrounding atmosphere can access and contact the indicator material.

For instance, the indicator material can be adhered to the surface of the carrier by means of an adhesive. In this case, it can be necessary to remove efflorescence of the deliquescent salt (c2) from the surface of the first fibrous sheet, if the indicator composition contains a combination of a water-soluble dye and a deliquescent salt, in order to provide for sufficiently strong adhesion.

Alternatively, the indicator material can be fixed on the carrier by clamping the edges of the indicator material with clamp-like features provided on the carrier.

The indicator material can also be covered and secured using a perforated membrane allowing the access of surrounding atmosphere to the indicator material, which perforated membrane is fixed to the carrier, for instance using an adhesive.

If the carrier itself is perforated such that surrounding atmosphere can access the indicator material, the indicator material could be fixed on the carrier using a transparent adhesive film covering the surface to be observed, i.e. the surface of the second fibrous sheet, wherein the transparent adhesive film itself does not have allow the access of surrounding atmosphere.

EXAMPLES

In the following, the present invention is illustrated by means of examples.

The following exemplary indicator compositions containing a water-soluble dye (c1) and a deliquescent salt (c2) are prepared by dissolving the amounts indicated in 10 ml of distilled water.

The limit value of the relative humidity for the detection of which the respective indicator composition is used is indicated in the third column.

Each of the aqueous solution of an indicator composition thus prepared is sprayed on a sample of a polyester nonwoven and the water is removed at a temperature of 80° C.

A filter paper having a weight of approximately 70 g/m² as the second fibrous sheet was placed on the surface of the dried polyester non-woven sample on which the hot-melt adhesive was provided. The sheets were laminated using an electric iron for domestic applications which was set to a temperature sufficiently high to activate the hot-melt adhesive and that was pressed on the filter paper.

Each of the indicator materials thus prepared was placed in a climate chamber set at 23° C. and the relative humidity indicated in the table hereinabove. After 2 hours the filter paper as the second fibrous sheet had been stained such that a positive result for the detection of elevated relative humidity was obtained.

| deliquescent salt [amount in g] | water-soluble dye [amount in mg] | relative humidity (%) |
|---|---|---|
| LiCl·H₂O [8] | Acid Blue 1 [15] | 15 |
| | Acid Violet 19 [15] | |
| | Acid Blue 9 [15] | |
| CaCl₂·6H₂O [6] | Acid Blue 1 [24] | 30 |
| | Acid Violet 19 [24] | |
| | Acid Blue 9 [24] | |
| NaBr·2H₂O [8] | Acid Blue 1 [15] | 60 |
| | Acid Violet 19 [15] | |
| | Acid Blue 9 [15] | |
| NH₄Cl [3] | Acid Blue 1 [15] | 80 |
| | Acid Violet 19 [15] | |
| | Acid Blue 9 [15] | |

The invention claimed is:

1. Indicator material suitable for detecting relative humidity exceeding a specific limit value and/or liquid water comprising
   (a) a first fibrous sheet,
   (b) a second fibrous sheet laminated to one surface of said first fibrous sheet by means of a hot-melt adhesive that does not cover the entire surfaces laminated to each other such that permeation of an aqueous solution from said first fibrous sheet to said second fibrous sheet is allowed, wherein said second fibrous sheet comprises cellulose fibres or cotton fibres, and
   (c) an indicator composition which comprises (c1) a water-soluble dye and (c2) a deliquescent salt, which composition is contained in said first fibrous sheet in finely divided form.

2. Indicator material according to claim 1, wherein the deliquescent salt is selected from the list consisting of LiBr.2H₂O, ZnBr₂.2H₂O, LiCl.H₂O, CaBr₂.6H₂O, LiI.3H₂O, CaCl₂.6H₂O, MgCl₂.6H₂O, NaI.2H₂O, K₂CO₃, NaBr.2H₂O, KI, NaCl, NH₄Cl, KBr, (NH₄)₂SO₄, KCl, CsI, K₂SO₄, potassium acetate and ZnSO₄.7H₂O.

3. Indicator material according to claim 1, wherein said water-soluble dye comprises a fluorescent dye.

4. Indicator material according to claim 1, wherein said water-soluble dye is selected from the group consisting of Acid blue 1, Acid blue 9 and Acid Fuchsine.

5. Indicator material according to claim 1, wherein said first fibrous sheet is non-woven.

6. Indicator material according to claim 1, wherein said first fibrous sheet comprises fibres prepared from a synthetic polymer.

7. Indicator material according to claim 6, wherein said synthetic polymer comprises a polyester.

8. An indicator device comprising the indicator material of claim 1 arranged on a carrier such that the surface of the second fibrous sheet of the indicator material can be observed, and the indicator material can be accessed by liquid water and/or elevated relative humidity that is present in the surroundings of the indicator device.

9. Indicator device according to claim 8, wherein the second fibrous material is arranged on the carrier as a blank.

10. A process for the manufacture of the indicator material of claim 1 comprising the steps of
    (i) providing a hot-melt adhesive on portions of one surface of a first fibrous sheet such that a regular or irregular geometric pattern of hot-melt adhesive is formed on the surface of the first fibrous sheet and the surface is laminated to the second fibrous sheet wherein the entire surface to be laminated is not covered with the hot-melt adhesive,
    (ii) impregnating the first fibrous sheet with a solution of an indicator composition which comprises (c1) a water-soluble dye and (c2) a deliquescent salt,
    (iii) removing solvent from the impregnated first fibrous sheet,
    (iv) laminating the second fibrous sheet to the first fibrous sheet by heating the hot-melt adhesive provided on the first fibrous sheet to a temperature sufficient to adhere to the second fibrous sheet,
    (v) pressing the second fibrous sheet onto the hot-melt adhesive, and
    (vi) cooling the hot-melt adhesive
wherein the solvent of the solution of an indicator composition used for impregnating the first fibrous sheet in step (ii) comprises water.

11. A process for the manufacture of the indicator device of claim 9, comprising
    (i) providing the indicator material as defined in claim 1,
    (ii) imparting a specific geometric shape to the indicator material, and
    (iii) arranging said indicator material on a carrier in such a manner that the surface of the second fibrous sheet of the indicator material can be observed, and the indicator material can be accessed by any liquid water and/or elevated relative humidity that is present in the surrounding of the indicator device.

* * * * *

UNITED STATES PATENT AND TRADEMARK OFFICE
CERTIFICATE OF CORRECTION

| | | |
|---|---|---|
| PATENT NO. | : 8,671,739 B2 | Page 1 of 1 |
| APPLICATION NO. | : 12/965035 | |
| DATED | : March 18, 2014 | |
| INVENTOR(S) | : Johanna Knyrim | |

It is certified that error appears in the above-identified patent and that said Letters Patent is hereby corrected as shown below:

Title page, item (73) Assignee, that portion of Assignee reading "Clariant Prosukte (Deutschland) GmbH," should read -Clariant Produkte (Deutschland) GmbH-.

Title page, item (74) Attorney, Agent, or Firm, that portion of attorney, agent or firm reading "Scoot R. Cox" should read -Scott R. Cox-.

Signed and Sealed this
Third Day of June, 2014

Michelle K. Lee
*Deputy Director of the United States Patent and Trademark Office*